United States Patent [19]

Harvey

[11] 4,342,836
[45] Aug. 3, 1982

[54] CONTINUOUS ANAEROBIC DIGESTOR SYSTEM

[76] Inventor: Christian D. Harvey, Bolduc Apts., Sandown Rd., Fremont, N.H. 03044

[21] Appl. No.: 197,978

[22] Filed: Oct. 17, 1980

[51] Int. Cl.³ .............................................. C12M 1/02
[52] U.S. Cl. ............................... 435/316; 48/197 A; 210/603; 308/101; 435/813; 435/801
[58] Field of Search ............... 435/166, 167, 316, 801, 435/813; 210/208, 603; 48/111, 197 A; 202/118; 308/101

[56] References Cited

U.S. PATENT DOCUMENTS

| | | | |
|---|---|---|---|
| 1,868,118 | 7/1932 | Rupp | 308/101 |
| 2,072,721 | 3/1937 | Rahm | 202/118 X |
| 2,538,412 | 1/1951 | Cecil et al. | 210/603 |
| 3,787,292 | 1/1974 | Keappler | 202/118 |
| 4,057,401 | 11/1977 | Boblitz | 435/166 X |
| 4,094,769 | 6/1978 | Brown | 202/118 X |
| 4,098,649 | 7/1978 | Redker | 202/118 X |
| 4,198,211 | 4/1980 | Shatlock | 435/167 X |
| 4,238,337 | 12/1980 | Peters et al. | 435/316 X |
| 4,248,972 | 2/1981 | Fischer et al. | 435/316 X |
| 4,252,901 | 2/1981 | Fischer et al. | 435/167 |

Primary Examiner—Robert J. Warden
Attorney, Agent, or Firm—John F. McClellan, Sr.

[57] ABSTRACT

An improved anaerobic digestor system for producing methane gas from waste biomass includes closed provisions for continuously feeding the biomass for system digestion, for continuously advancing and stirring the biomass while in the system through a continuum of stages, for continuously collecting gases produced and for continuously expelling spent biomass from the system for use as fertilizer; a second embodiment provides a longer path in a plurality of parallel short length troughs cast in one piece, each trough of which has a corresponding plurality of hemi-cylindrical covers and of end pieces with "U" shaped connections between ends of the tanks so-formed.

15 Claims, 7 Drawing Figures

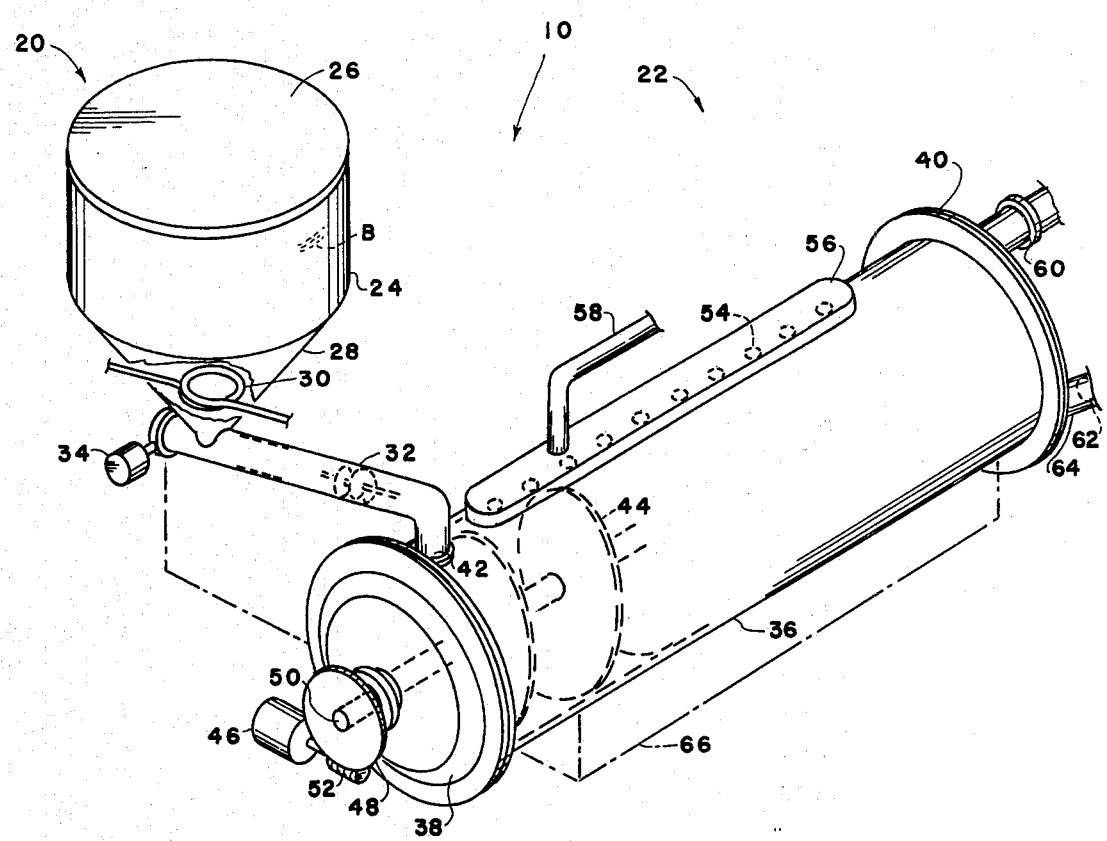
FIG. 1
FIG. 2
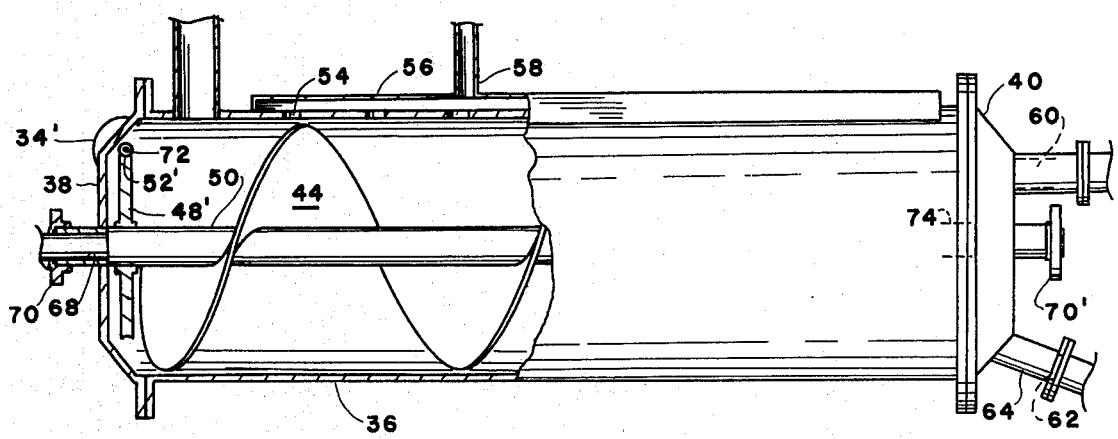

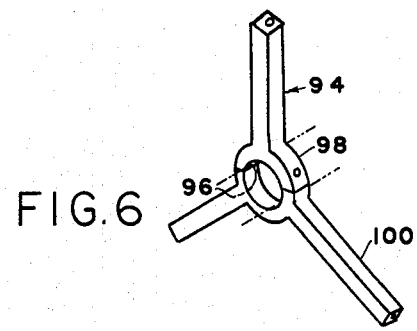
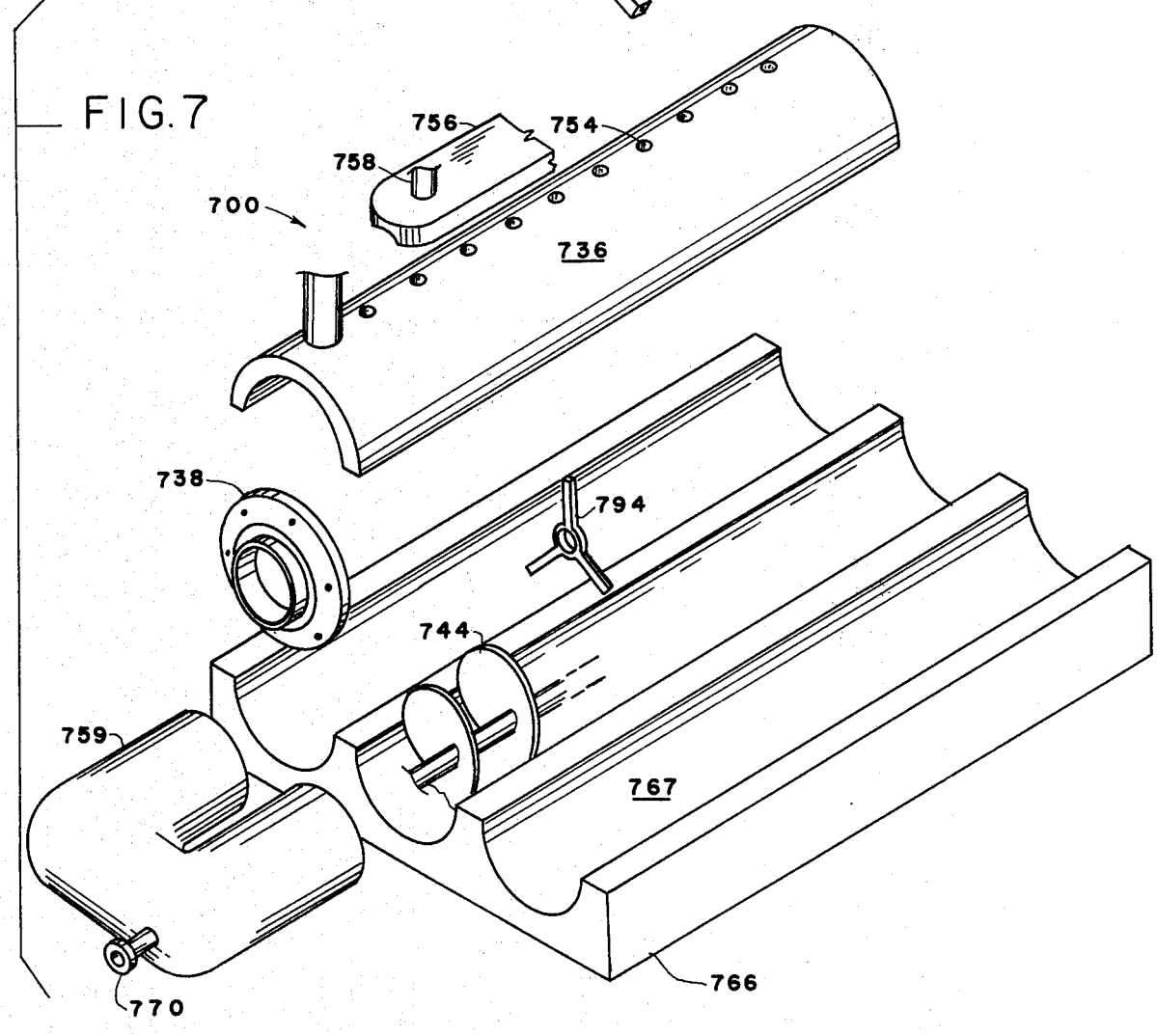

CONTINUOUS ANAEROBIC DIGESTOR SYSTEM

This invention relates generally to combustible gas production systems and specifically to an improved anaerobic digestion system.

BACKGROUND OF THE INVENTION

Anaerobic fermentation of wastes has been in use for more than one hundred years; it is estimated "that this clean renewable source of energy could supply a large fraction of the energy used in farming operations and that if marginal lands were used to produce biomass for fuels, the entire U.S. energy demand could be met". The preceding information comes from the abstract of W. J. Jewell et al, *Bioconversion of Agricultural Wastes For Pollution Control And Energy Conservation*, Final Report Contract ERDA-NSF-741222A01, Cornell University, September 1976. This report discloses various systems for digestion of organic wastes including semi-continuous feed employing silo apparatus, completely mixed systems, "continuous" feed or MUNICH systems, batch load systems and plug flow systems and permutations and combinations of these, heated and unheated.

The following U.S. Pats. deal with digestion of organic wastes over a span exceeding one hundred years; some disclose gas production:

No. 39,472 to R. B. Fitts, 8-11-1863, discloses gas production in night soil treatment;

No. 39,525 to P. Eley, 8-11-1863, discloses screening and fermenting treatment of night soil;

No. 1,543,154 to C. B. Fox et al, 6-23-25 discloses fine grinding organic waste and fermenting it;

No. 1,963,581 to H. Henkelekian, 6-19-34, discloses anaerobic production of methane and thermal selection of bacteria strains;

No. 2,755,293 to D. McDonald, 7-17-56, discloses a centrifuge employed in a system having screw feed of waste organic materials being processed;

No. 3,241,943 to S. G. Bystrom, 3-22-66, discloses a gas producing sewage system treatment employing a plurality of containers in stages;

No. 3,890,129 to F. B. Chester, 6-17-75, discloses a composting device employing rotary mixing;

No. 4,040,953 to J. E. Ort, 8-9-77, discloses an anaerobic system for production of methane by a two stage system.

A. Makhijani et al, *Energy And Agriculture In The Third World*, Bollinger Publishing Company, date not available, but 1974 or later, discusses aspects of gas production from organic wastes including separating stages of digestion, heating considerations, vertical mixing systems, linear displacement plug flow canal systems with different stages of digestion at different points along the length of the canal, and the possibility of mixing in a canal system.

General requirements for the economic production of methane from waste biomass can be summarized with reference to the foregoing sources of information:

1. Mixing: methane production is optimized if waste slurry is continuously mixed (Bystrom patent and Chester patent);

2. Heating: methane production is optimized if the slurry mixture is maintained between 30° C. and 35° C. for mesophilic digestion (Bystrom patent and Chester patent), and between 50° C. and 60° C. for thermophilic digestion (Jewel et al publication).

3. Continuous flow: Although numerous batch type digestors have been patented and used, the labor costs and health and odor problems of batch processes make continuous flow highly desirable (Jewell et al publication).

4. Minimum Size: The material and equipment costs of a digestor scale nearly linearly with size. Thus for minimum costs, it is desirable to have limited dilution of the waste material.

5. Simplicity: The operators of digestor systems normally do not have engineering degrees to say the least. Thus the simpler the system, the better.

6. Reliability: The digestor and its supporting equipment should be capable of operating reliably under adverse conditions. Typical unintended contaminants include stones, wood chips, gravel, etc. The digestor and the charging and discharging system (pumps, et.) must be capable of handling such foreign objects with minimum risk of breakdown. (Jewell et al publication).

The digestor must also be capable of operating under variable environmental conditions, especially cold weather.

Digestor systems developed to date address one or more of the above requirements but none has provided a simultaneous solution to all requirements. Early patent literature (patents to Fitt, Eley, Fox et al, Henkelekian) describes batch type digestors which only signify that methane can be produced from farm and municipal wastes. The Fox et al patent recognizes the advantage of pregrinding waste material. The Henkelekian patent describes a batch digestor which used a portion of the methane produced to heat the tanks. The McDonald patent describes a continuous flow digestor requiring significant dilution (large size).

The Ort patent describes a continuous flow digestor (using dilute slurries) that has two stages. Continuous mixing is accomplished in the first stage. The McDonald patent describes a continuous feed system for on-farm use with several chambers. These last two systems through approaching the total solution, have several drawbacks. Both use dilute slurries to minimize pumping/mixing problems; as a consequence, system volume and therefore cost are considerably increased. They both suffer from difficult maintenance problems in the event of pump failure, and both require periodic shutdown and cleanout to prevent buildup of foreign matter.

The Makhijani publication states that a linear displacement digestor is the most prominent candidate to reduce costs. In his design, a long canal approximates plug flow (also recommended in the Cornell study). Difficulties are anticipated, however, in maintaining flow in such a system.

In summary, it is believed that no system has been previously disclosed which provides the advantages of the present system according to the objects of this invention, among which are:

to provide a system for gaseous fuel production by anaerobic digestion of waste biomass, which combines the advantages of multi-stage-digestion efficiency with the simplicity of single stage apparatus, and which affords reliability and performance suitable for long-term trouble-free use in primitive areas as well as in areas where extreme efficiency and highest quality in methane gas production are the primary goals;

to provide a system as described which is at all times substantially self-cleaning, and self-clearing of stones and other undigestible ingestants;

to provide a system as described which can process biomass or waste material efficiently at both high and low solids concentration, and in both the mesophilic and the thermophilic ranges.

BRIEF SUMMARY OF THE INVENTION

In brief summary the invention includes a closed linear system for constant low-speed advancing of waste organic material from a continuous feed at the ingress to continuous exhaust at the egress. The central screw conveyor provides continuous mixing and effects a uniform progression of digestive stages along the system, while allowing the gases produced to be collected simultaneously.

The above and other objects and advantages of this invention will become more readily apparent upon examination of the following description, and drawings, in which like characters refer to like parts.

BRIEF DESCRIPTION OF THE FIGURES

FIG. 1 is a perspective view of the invention incorporated in a first embodiment;

FIG. 2 is an elevational detail in partial longitudinal section of the first embodiment;

FIG. 6 is a perspective view of a structural spider member; and

FIG. 7 is a perspective diagram of a second embodiment in exploded view.

DETAILED DESCRIPTION OF THE FIGURES

Figure 3:
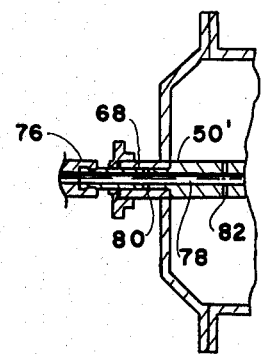
FIG. 3 is a fragmentary detail in partial longitudinal section of an end portion of an optional provision.

FIG. 1 shows the simplest embodiment 10 of the invention, an improved system for anaerobic digestion of organic material to produce methane gas and useful solid and liquid fertilizing materials from waste biomass.

The embodiment comprises a feeder unit 20 and a digestor unit 22. The feeder unit or reservoir is a means for continuously receiving and feeding biomass or waste organic material into the system and may comprise a feed tank 24, preferably with a closable top 26 and having a funnel shaped lower portion 28 with tubing coils 30 or equivalent for heating the biomass B with steam or other hot fluid. If desired, steam may be flowed upwardly through the biomass. The system is continuously charged as the biomass passes down under gravitational force into the intake end of a first conveyor 32 which preferably is a substantially horizontal screw conveyor. The first conveyor preferably is a closed tube sealed at the first end at the conventional motor drive 34, sealed at the intake from the tank, and sealed at the second end or exhaust into the digestor unit.

The digestor unit continuously processes organic material through the system and includes a cylindrical tank-comprising means or chamber body 36 and first and second end caps 38, 40. The digestor unit entrance port or intake 42 from the feeder unit is preferably in the upper portion of the first end of the body. From that point a second screw conveyor 44 axially mounted in the body and of a length and diameter to fill the body substantially so that the biomass taken in is efficiently and simultaneously moved at a uniform rate throughout the length of the body.

The motor drive 46 is similar to that of the first, and proportionally turns the second screw conveyor at a slow rate.

The screw of the second conveyor may advantageously be rotated by means of a worm gear 48 on the shaft 50 of the screw means outside the first end cap and driven by a worm 52 on the shaft of the motor 46, which may be an electric motor with frame attached to the end cap. The biomass can thus be kept from the drive.

As the biomass moves along the body in this sealed system it is continuously mixed, ferments and gives off gases, primarily methane and carbon dioxide, sealed in together and collected through perforations 54 along the length of the body into a manifold 56 which vents to a conventional gas accumulating tank (not shown) through a pipe 58.

Speed and lead of the screw are made to be such as to advance the biomass through the system on a schedule adopted according to well known principles to yield the greatest quantity of methane. The most efficient length of time is determined by the temperature, pressure, and liquid proportion and other constituencies of the biomass, and other known parameters.

To assist in the process, fluid (water and/or steam for example) may be added to the system, and the body may be continuously heated and insulated to retain the heat, as described below. At the second end cap the system continuously discharges effluent, which may consist of both solid and liquid residues of the biomass and fluids associated with the process.

The exhaust port 60 for the effluent is preferably at the top, where the screw-imposed pressure of the system forces it out. Foreign matter such as rocks may be expelled downward from a lower or debris expulsion port 62 which has ante-room 64 to accumulate the debris. When this port is opened for an interval the contaminants may be manually or automatically cleared.

The system may rest on laid footings 66 or any sound foundation such as a poured foundation.

FIG. 2 shows further details of the system. The second screw means 44 has bearings supporting it, which may be in the tubular body portion or in the end caps. The bearing 68 in the first end cap 38 being shown here as an ordinary thrust bearing adjacent a conventional packing gland 70 that seals the shaft rotational movement against leakage.

As an optional feature, the motor 34' for the screw drive may be on the outside but with the motor shaft 72 extending through a conventional gland to the inside of the end cap where the worm 52' on the end of the motor shaft tangentially engages a worm gear 48' fixed on the screw shaft 50.

This figure also shows the gas collection arrangement including perforations or holes 54 in the top of the cylindrical wall of the body 36 and over all these the manifold 56 and pipe 58 which conduct the gas off to storage. At the top of the second end cap 40 is the effluent exhaust port 60 and tubular line for conducting the effluent to a storage area, and further at the bottom of the second end cap is the debris collector portion 64 and exhaust 62. Bearing 74 and gland 70' for the screw in the second end cap may be similar to that in the first end cap.

FIG. 3 shows an optional arrangement in which fluid such as steam or water under pressure may be introduced into the digestor through a conventional rotary seal 76 into an end of the screw shaft 50'. This shaft has an axial bore 78 for the purpose. The steam or water passes through holes 80 within the bearings (68 shown) for flushing the bearings clear of the biomass slurry at all times, easing operation and relieving maintenance needs. The fluid itself may act as a greaseless bearing lubricant, and additionally as a heating agent and diluent for the biomass. Further, for the latter two purposes, additional fluid may be emitted through additional sets of radial holes 82 in the screw shaft free of the bearings.

Figure 4:
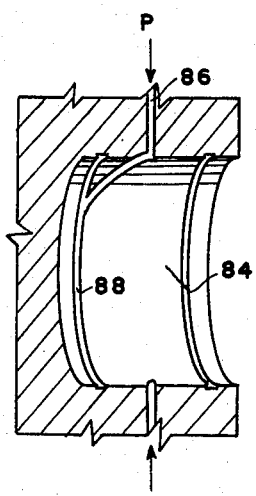
FIG. 4 is an enlarged fragmentary detail showing an optional bearing provision.

FIG. 4 is a fragmentary detail of an alternative provision for flushing the bearings, 84 shown, with fluid through bores 86 in the fixed structure supporting the bearings. The bores are connected with a pressure source of the fluid represented by P and arrows, to flush the bearings by connection with grooves 88 forming a ring at each end of the bearing.

Figure 5:
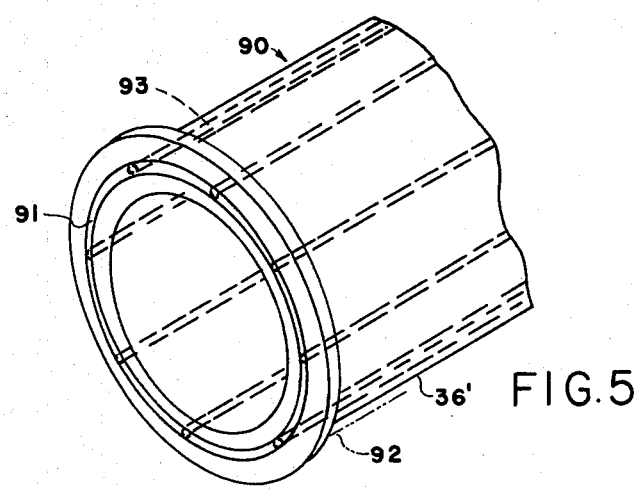
FIG. 5 is a fragmentary perspective diagram of an optional provision.

FIG. 5 shows that a loop network 90 of pressure fluid passageways or heat emitting areas may be fashioned in the walls of the body 36'. These may be in ring groove 91 and plural-stringer-bore 93 arrangement for even distribution of heating fluid passed through them using heat generated from the gases collected from said digestion. The digestor body, bores, and the other parts of the system may have insulation 92 applied on the exterior to aid in heat retention.

FIG. 6 shows a typical spider support 94 which may be used along the length of the second screw conveyor means to support respective bearing surfaces 96 of the screw shaft. They may be assembled to the spiders at the ends and or at intermediate locations if desired.

Preferably each spider comprises a ring 98 axial to the bore of the body when installed and supported by three radial legs 100 integral with the ring. The ends of the legs, especially the two lower legs, may be embedded in or attached by screws to the body; it is evident that in accordance with conventional practice the ring may be made of two hemi-rings screwed together detachably for assembly to the screw conveyor bearings. At each spider location the screw conveyor flanges may be interrupted but pass in rotation close to the spider on either side, producing desirable shearing forces on the biomass urged along through the spacings in the spiders.

SECOND EMBODIMENT

FIG. 7 diagrams a second embodiment 700 of the invention in which the base 766 of the bodies comprises preferably a concrete member with a plurality of upwardly concave hemi-cylinders 767 in it. To cover the hemi-cylinders and form cylindrical tank or chamber bodies for the respective screws 744 of the conveyor mechanism a matching or complementary plurality of hemi-cylindrical covers 736 is provided. Each cover is the same length as the troughs and attached to the base by cement, or by screws or other suitable means. Rows of perforations 754 along the tops of these provide for gas to pass upward for collection by similarly attached manifolds 756 on the covers and pipes 758 from the manifolds to storage.

End caps 738 and spiders 794 may be supplied as before, except that "U" tube connections 759 joining adjacent ends of the bodies may be used for connection of the units in series or in series-parallel. The "U" tubes may be of metal or of heavy wall elastomeric material of conventional composition, and may be of full tube diameter and may be attached by screws or cement. Drive to the shaft may be similarly through packing glands 770 in the "U" tubes. Other connections and drive and operation of these economical units may be as described before.

It will be evident that the cast base can provide alignment for the units permitting multiple drive from a single power source if desired, according to known mechanical linkages, and further evident that the slow rotational speeds and covered construction make for safety and reliability.

Methane gas produced can be employed to run an onsite diesel generator. The waste heat of the diesel can be used to heat both the input fluid and the temperature maintenance fluid for the generator.

A small accumulator of conventional design may be used in the gas collection pipe to separate the vaporous constituents by well-known principles. $CO_2$ can be removed by a conventional bubble chamber or known membrane technology. Such removal is not required, however.

It will be appreciated that the end bearings of the second screw conveyor can be mounted in the end caps, and that other such variations on invention may be employed without departing from the spirit. A conventional gate valve can be used for ejection of debris from the digestor.

SPECIFIC EXAMPLE

A 100 head dairy herd produces approximately 154 cu. ft. of manure per day. Using a 10 day hydraulic retention time, the volume of a mesophilic digestor would have to be 1540 cu. ft. with no dilution. This could be accommodated and staged by a 10 ft. diameter digestor 20 ft. long (volume 1570 cu. ft.) allowing for minor dilution. The construction of the tubular portion of the digestor could be cement, fiber reinforced polypropylene, fiberglass or metal. The end caps could be molded or cast with similar materials. Bearing inserts and flange plates could be of stainless steel directly imbedded in the casting or molding; replaceable bearing inserts could also be considered. The auger could be constructed using an aluminum or steel substrate covered with a thin layer of fiberglass. The gas accumulator could be separately fabricated and bolted to the top of the digestor, using a non-reactive seal such as Teflon. Delivered costs for this portion are estimated to be $20,000 or less, depending on the final materials selected for construction. This cost would include drive motors, feed tank, and gas pump. The 154 cu. ft. per day would contain 1007 pounds of volatile solids. With a ten day HRT (hydraulic retention time) it is expected that a 40% reduction in volatile solids would occur with average production of 7300 cu. ft. per day of methane/$CO_2$ gas produced at a ratio of 1.86, and a heating value of 650 BTU/ft.$^3$. Thus a total of 4,750,000 BTU per day or 198,000 BTU/hr would be produced. On such a farm the peak electrical load is about 15 kw with an average load of 6 kw. The estimated maximum power required to run the digestor and pump is 1.3 horsepower or 1.0 kw. Thus a 15 kw diesel powering an alternator of 90% efficiency, would satisfy for the farm's electrical demand. Operating at average load of about 7 kw (6 kw average for farm plus a 1.0 kw digestor) the diesel would perform at about 25% efficiency. A waste heat boiler operating at 50% efficiency would produce about 18 pounds per hour of 5 psi steam, adequate to heat the digestor and feed completely with excess steam available. At average load (7 kw) the diesel would consume 105,430 BTU/hr leaving excess gas of 90,000 BTU/hr available. The diesel is estimated to cost $8,500 and the gas handling and storage facilities $1,000.00. Total system cost would be about $30,000. The value of the excess gas produced at $2.50 per million BTU would be $1,800 per year. The value of the electricity over and above the digestor demand would be $1,980 (at 4 cents per kwh) for a total annual return of $3,720.

The stabilized effluent from the digestor (which is virtually odorless) would contain (on a yearly basis) about 2.0, 0.9, and 1.7 tons of nitrogen, phosphorous, and potassium, respectively, sufficient to fertilize 30 acres of corn (with no rotation) at an approximate annual value of $2,000.

The total return on the investment is equal to $1,800 plus $1,980 plus $2,000, or $5,780 per year, based on current energy prices. This would give a simple payback period of 5.2 years. A more sophisticated analysis uses the following assumptions:
Cost of investment: $30,000
Discount Rate: 15%
First year's savings: $5,780
Annual operating cost: $500
Energy inflation rate: 10%
Life of system: 15 years An iterative financial analysis shows this investment to have a 2.3 year payback period with a return on investment of 36%.

Using thermophilic digestion, the size and hence capital cost would be reduced. Detailed data on thermophilic digestion is not yet available, but it is estimated that digestor costs could be reduced by as much as $8,000, making the potential simple payback less than 2 years.

This invention is not to be construed as limited to the particular forms disclosed herein, since these are to be regarded as illustrative rather than restrictive. It is, therefore, to be understood that the invention may be practiced within the scope of the claims otherwise than as specifically described.

What is claimed and desired to be protected by United States Letters Patent is:

1. In a system for anaerobic digestion of organic material to produce methane gas, the improvement comprising in combination: means for continuously feeding said organic material into said system, means for continuously processing said organic material through the system; means for continuously receiving said gases from the system; means for continuously discharging effluent from the system, the means for continuously processing including horizontally disposed cylindrical tank-comprising means, screw means axially mounted therein, means defining an entrance port at a first end portion of the cylindrical tank-comprising means; the means for continuously discharging effluent being means defining an exhaust port at a second end portion of the cylindrical tank-comprising means, the means for continuously processing further including means for continuously rotating the screw means in a direction for urging said organic matter from the entrance port to the exhaust port, the means for continuously rotating comprising motor means having attachment to the screw means, said screw means mounting including a plurality of bearings having respective supports to said cylindrical tank-comprising means, means for supplying a fluid to said organic material to facilitate said anaerobic digestion; and means for protecting said plurality of bearings from damage by intrusion therein of said organic material continuously processed, including means for injecting a fluid from outside the cylindrical tank-comprising means into the plurality of bearings and for expelling said fluid from the plurality of bearings within the cylindrical tank-comprising means, said fluid supplied being said fluid expelled from the plurality of bearings within the cylindrical tank-comprising means.

2. In a system as recited in claim 1, said plurality of bearings including thrust bearing means at said first end of the cylindrical tank-comprising means, and means for causing mixing by shearing of said organic material, comprising said support including at least one mount having legs radiating from a bearing adjacent an end of the screw means, said mount being affixed to the cylindrical tank comprising means with the bearing supporting the screw means.

3. In a system as recited in claim 2, a plurality of said mounts interspersed between the ends of a plurality of said screw means.

4. In a system as recited in claim 1, the means for continuously processing including horizontally disposed cylindrical tank-comprising means and solid debris downward discharge means apart from said means for continuously discharging effluent, the means for continuously discharging effluent being in an upper portion of the cylindrical tank-comprising means, and the solid debris downward discharge means being in a lower portion of the cylindrical tank-comprising means, below the means for continuously discharging.

5. In a system as recited in claim 1, the means for continuously receiving said gases from the system including structure defining a plurality of holes along the upper part of said cylindrical tank-comprising means, a manifold over said plurality of holes, and a duct connecting with the manifold for transporting said gases from the system.

6. In a system as recited in claim 1, the cylindrical tank-comprising means including: a base forming at least one hemicylindrical trough, at least one cover having a hemicylindrical portion proportioned for affixation on the base and forming a tube, and a plurality of end members for closing the respective ends of said tube.

7. In a system as recited in claim 6, said base forming a plurality of said hemicylindrical troughs side-by-side in parallel spacing, and a plurality of covers over the respective hemicylindrical troughs.

8. In a system as recited in claim 7, at least part of said plurality of end members being "U" shaped tubes respectively connecting the plurality of hemicylindrical troughs.

9. In a system as recited in claim 8, said connection being in series.

10. In a system as recited in claim 8, said connection being at least in part in parallel.

11. In a system as recited in claim 7, said base being of cast concrete.

12. In a system as recited in claim 1, the means for continuously feeding including: a reservoir, closed screw conveyor means for conveying organic material from the reservoir to the cylindrical tank-comprising means, the closed screw conveyor means passing from the bottom of the reservoir to a top portion of the cylindrical tank-comprising means, and means for ejecting steam upwardly through said organic material located immediately above the screw conveyor means at the bottom of the reservoir.

13. In a system as recited in claim 12, means adapting said system alternatively for mesophilic digestion and for thermophilic digestion, including the means for receiving gases from said system having connection for processing said gases for heat generation therefrom, and the cylindrical tank-comprising means including connection therewith through a series of emitting areas for said heat around and along the cylindrical tank-comprising means.

14. In a system for anaerobic digestion of organic material to produce methane gas, the improvement comprising in combination: means for continuously feeding said organic material into said system, means for continuously processing said organic material through the system; means for continuously receiving said gases from the system, means for continuously discharging effluent from the system; the means for continuously processing including horizontally disposed cylindrical tank-comprising means, screw means axially mounted therein, means defining an entrance port at a first end portion of the cylindrical tank-comprising means; the means for continuously discharging effluent being means defining an exhaust port at a second end portion of the cylindrical tank-comprising means; the cylindrical tank-comprising means including: a base forming a plurality of said hemicylindrical troughs side-by-side in parallel spacing, a plurality of covers over the respective hemicylindrical troughs; and said base being of cast concrete.

15. In a system for anaerobic digestion of organic material to produce methane gas, the improvement comprising in combination: means for continuously feeding said organic material into said system, means for continuously processing said organic material through the system; means for continuously receiving said gases from the system, means for continuously discharging effluent from the system; the means for continuously processing including horizontally disposed cylindrical tank-comprising means, screw means axially mounted therein, means defining an entrance port at a first end portion of the cylindrical tank-comprising means; the means for continuously discharging effluent being means defining an exhaust port at a second end portion of the cylindrical tank-comprising means; the means for continuously processing further including means for continuously rotating the screw means in a direction for urging said organic matter from the entrance port to the exhaust port; the means for continuously rotating comprising motor means having attachment to the screw means, said screw means mounting including a plurality of bearings having support to said cylindrical tank-comprising means, the means for continuously receiving gases from said system having connection for processing said gases for heat generation therefrom, and the cylindrical tank-comprising means including connection therewith through a series of emitting areas for said heat around and along the cylindrical tank-comprising means.

* * * * *